United States Patent [19]

Holmes

[11] Patent Number: 5,647,663
[45] Date of Patent: Jul. 15, 1997

[54] RADIATION TREATMENT PLANNING METHOD AND APPARATUS

[75] Inventor: Timothy W. Holmes, Madison, Wis.

[73] Assignee: Wisconsin Alumni Research Foundation, Madison, Wis.

[21] Appl. No.: 583,388

[22] Filed: Jan. 5, 1996

[51] Int. Cl.$^6$ .................................................. G06F 15/00
[52] U.S. Cl. ........................................ 128/653.1; 128/922
[58] Field of Search ......................................... 128/413.26

[56] References Cited

U.S. PATENT DOCUMENTS

| | | |
|---|---|---|
| 3,206,893 | 9/1965 | Hara . |
| 3,871,579 | 3/1975 | Inamura .............. 364/413.26 |
| 3,987,281 | 10/1976 | Hodes ................. 364/413.26 |
| 4,729,099 | 3/1988 | Iverson et al. ........ 364/413.26 |
| 5,205,289 | 4/1993 | Hardy et al. . |
| 5,291,404 | 3/1994 | Kurokawa et al. . |
| 5,373,844 | 12/1994 | Smith et al. .......... 364/413.26 |
| 5,418,827 | 5/1995 | Deasy et al. .......... 364/413.26 |

*Primary Examiner*—William E. Kamm
*Attorney, Agent, or Firm*—Quarles & Brady

[57] ABSTRACT

A method of radiation treatment planning for radiation systems providing multiple beams of independently adjustable intensities limits the iterative beam weight determination to a set of discrete beam weights avoiding errors in post-optimization truncation of the beam weights, and decreasing the iteration time. Those beams having a greatest effect on the solution are preferentially adjusted and larger changes between discrete values of beam weights are given preference to smaller changes.

12 Claims, 2 Drawing Sheets

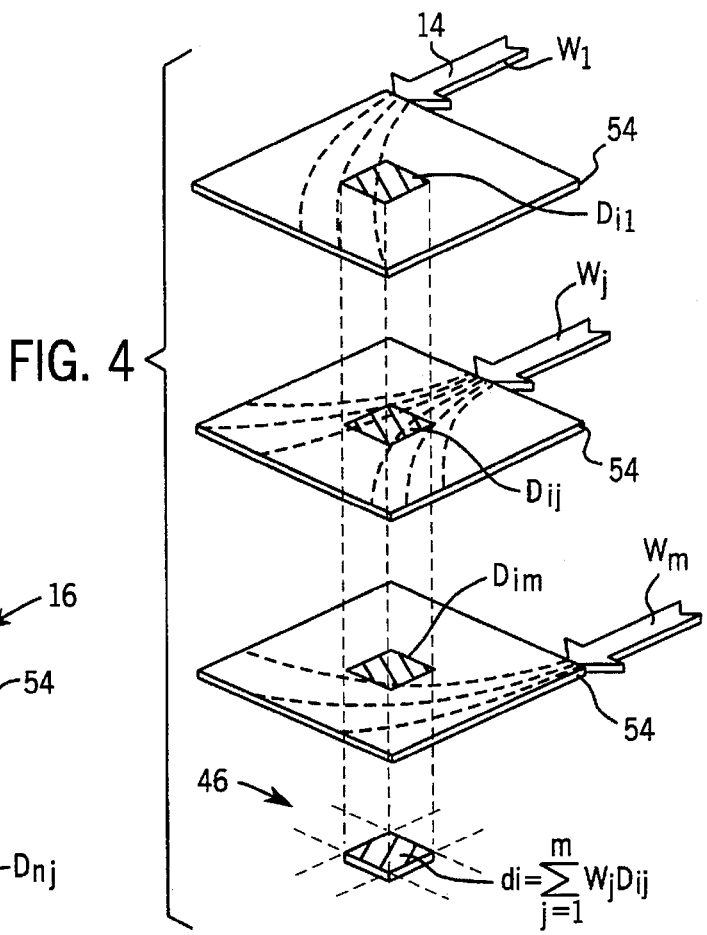
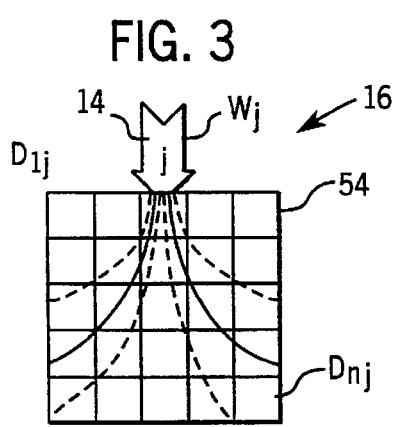
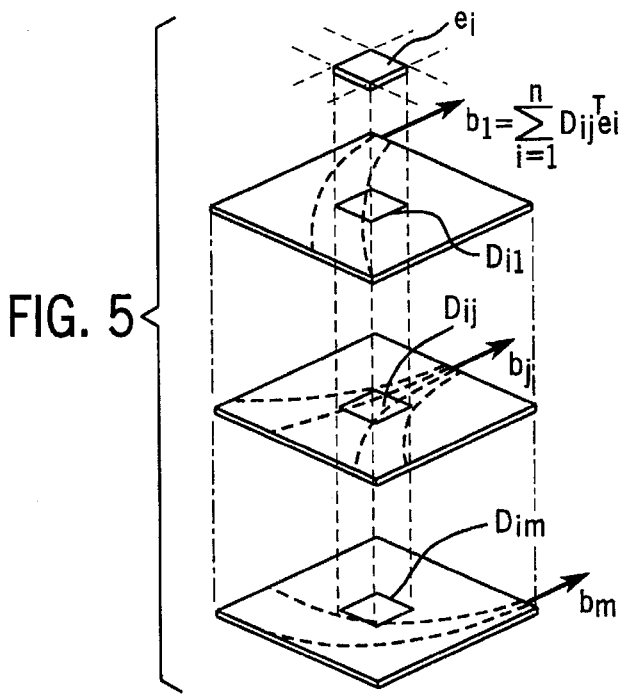

RADIATION TREATMENT PLANNING METHOD AND APPARATUS

FIELD OF THE INVENTION

This invention relates generally to radiation therapy equipment for the treatment of tumors, or the like, and specifically to a computerized method for determining the intensity of multiple x-ray beams so as to accurately place radiation dose in a patient.

BACKGROUND OF THE INVENTION

Medical equipment for radiation therapy treats tumorous tissue with high-energy radiation. The amount of radiation and its placement must be accurately controlled to ensure both that the tumor receives sufficient radiation to be destroyed, and that the damage to the surrounding and adjacent non-tumorous tissue is minimized.

External source radiation therapy uses a radiation source external to the patient to treat internal tumors. The source of high-energy radiation may be x-rays, or electrons from linear accelerators in the range of 2 to 25 MeV, or gamma rays from highly focused radioisotopes such as a $Co^{60}$ source having an energy of 1.25 MeV.

The external source is normally collimated to direct a beam only to the tumorous site. Typically, the tumor will be treated from several different angles with the intensity and shape of the beam adjusted appropriately. Using multiple beams which converge on the site of the tumor reduces the dose to particular areas of the surrounding tissue. The angles at which the tumor is irradiated may be further selected to avoid the irradiation of radiation sensitive structures near the tumor site.

A highly accurate method of controlling the dose to a patient employs a radiation source that produces a fan beam composed of many individual rays whose intensity may be independently controlled. The fan beam orbits the patient within a slice plane illuminating a slice of the patient while the intensity of each ray of the fan beam is changed as a function of that angle. By properly selecting the beam intensities at different angles, complex regions within the slice may be accurately irradiated. U.S. Pat. No. 5,317,616, issued May 31, 1994 and assigned to the same assignee as the present application, describes the construction of one such machine and one method of calculating the necessary beam intensities as a function of angle.

As mentioned, with such machines, the dose at any given volume within the patient will be derived from a number of different beams irradiating that volume at different angles. Each beam passes both through the tumor and through tissue on either side of the area to be irradiated. Beams which pass through tissue flanking the tumor and highly sensitive to radiation, are decreased in intensity. Other beams passing through less sensitive tissue are increased in intensity to maintain the dose to the tumor.

Determining beam weights for a desired dose pattern is normally done by an iterative technique, where particular beam weightings are evaluated by mathematically modeling the expected dose. The beam weights are then adjusted and the model is evaluated to see if it is closer to the desired dose. This process is repeated many times until the computed dose pattern closely approximates the desired dose pattern. The resulting beam weights are recorded and used for the radiation therapy. Generally, the changes in the beam weights between iterations are random and hence the process may be broadly characterized as stochastic.

In a "simulated annealing" stochastic technique, (so-called because of its mathematical similarity to the process of annealing metal) a new set of beam weights is always adopted, in the iterative process, if it results in an improvement in the computed dose distribution d as measured by a figure of merit of the computed dose f(d) called the "objective function". On the other hand, a new set of beam weights which results in a worse computed dose than the previous result may be adopted with a small probability. This probability is expressed by the function $\exp(-\Delta f(a)/T)$, where $\Delta f(a)$ is the change in the objective function from one iteration to the next, and T, called the "temperature" is progressively reduced as the number of iterations increases, thereby reducing the probability of accepting worse solutions as measured by the objective function. The purpose of probabilistically accepting worse solutions is to allow the iterative procedure to escape from "local minima" of the objective function space, (corresponding to locally optimal solutions) and to continue onward toward determining the best possible solution associated with the smallest objective function, commonly referred to as the "global minimum". See, generally, Webb, S. *Optimization by Simulation Annealing of Three Dimensional Conformal Treatment planning for Radiation Fields Defined by a Multi-Leaf Collimator*, Phys. Med. Biol. 36 1201–26, 1991.

Another stochastic technique is the so-called "genetic algorithm". During each iteration, the genetic algorithm samples a population of solutions from which a subpopulation of best solutions is chosen based on the match between the computed dose and the desired dose. A new population of solutions is bred from random pairs of members of the subpopulation using techniques called "cross over" and "mutation." The population of solutions rapidly "evolves" towards one whose members, although not necessarily identical, share many characteristics of the globally optimal solution. See, generally, Goldberg, D. E., *Genetic Algorithms in Search, Optimization and Machine Learning*, Addison Wesley (1989).

Millions of iterations may be required to reach acceptable solutions with these techniques. As a result, the radiation planning process is delayed and the planning physician is discouraged from varying the initially selected dose pattern by the lengthy time needed for a recalculation.

SUMMARY OF THE INVENTION

The present invention exploits the practical inability of radiation therapy equipment to provide more than a relatively small set of discrete intensity values. By incorporating a "discretization" of the intensity values of the radiation beams used in the iterations, the number of iterations required may be reduced and any errors produced by after-the-fact truncation of a continuous solution to discrete values are eliminated. For example, if the radiation therapy equipment can provide only six intensity values for each beam, then the present invention examines only combinations of these discrete beam intensity values.

The present invention, in selecting beam weightings to be evaluated in the iterative process, concentrates changes in the beam weights to beams that have the most effect on the objective function that is being optimized. The changes are also biased toward larger increments of beam intensity. Thus a completely random selection of beam weightings is avoided.

To further speed the determination of an optimal set of beam weights, the present invention also pre-computes the radiation scattered by each beam. In this way, during the iterative process, computed dose may be rapidly determined by a simple scaling and superposition rapidly performed by current electronic computers.

Specifically, then, the method allows treatment planning for a general radiation therapy machine providing a plurality of individually controllable radiation beams directed through a treatment volume. In a first step of the method, the user defines a limited set of discrete intensity values to which each beam will conform. The user then provides an objective function of the computed dose which mathematically describes the clinical objectives of the treatment which one is trying to achieve. From an initial weight for each beam, a computed dose map is then computed and the objective function value is determined for the computed dose map. This value of the objective function is compared to the previous objective function value. Based on this comparison, the initial weights of the beams are adjusted, but only to different ones of the discrete intensity values. The process is repeated until the change in the objective function is within an acceptably small tolerance defined by the user or the computed dose falls within acceptable limits defined by the user.

Thus, it is a first object of the invention to take into account actual or effective limitations in the radiation therapy equipment that limit the number of different intensities it can produce. By limiting the optimization B process to previously determined discrete values (rather than truncate the answer to those values) the number of iterations needed to produce a solution may be reduced and errors which might result from a truncation of an optimized set of beam weights to the discrete values are avoided.

The method may include the additional steps of determining at least one beam or a subset of beams having the greatest effect on the objective function. In the adjustment of the initial weight of the beams, the beam or beams having the greatest effect on the objective function is given preference.

Thus, it is another object of the invention to improve upon a strictly random examination of solution space such as is provided by some stochastic methods. The determination of the beam having the greatest effect on the objective function is a simple process and may be used to either adjust that beam first or to statistically bias the adjustment process toward adjusting that beam instead of the other beams, thus reducing the number of iterations necessary to find an optimal solution.

In the method, the adjustment of the initial beam weights to the discrete intensity values may prefer adjustments that cause greater change to the beam weight.

Thus, it is another object of the invention to improve over a strictly random selection of adjustment amounts in seeking a solution. By biasing the selection of adjustment amounts (between the discrete values) to larger amounts, rapid convergence on a solution may be obtained. A normal "temperature" factor, which decreases with increasing iterations, is used to prevent the large changes from disrupting the solution near the end of the iteration cycle.

The determination of the computed dose may be performed by separately pre-computing a reference dose map for a plurality of the volume elements within the treatment volume for each individual beam with the beams assumed to have a predetermined normal beam intensity. The reference dose maps indicate the radiation scatter pattern for each beam. As the initial weights for each beam are changed, the pre-computed dose map for each beam is scaled, and the scaled dose maps are summed together to produce a computed dose map.

Thus, it is another object of the invention to improve the speed of the iterative process as executed on a standard electronic computer.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 3 is a representation of an array stored in computer memory defining the dose and scatter of a single pencil beam of normal intensity for an example two dimensional treatment area;

FIG. 4 is a schematic representation of the summing together of scaled values from a number of arrays such as that shown in FIG. 3 to rapidly determine dose from multiple pencil beams; and FIG. 5 is a figure similar to that of FIG. 4 showing the identification of the beam having the most effect on the objective function.

DETAILED DESCRIPTION OF THE PREFERRED EMBODIMENT

System Hardware

Figure 1:
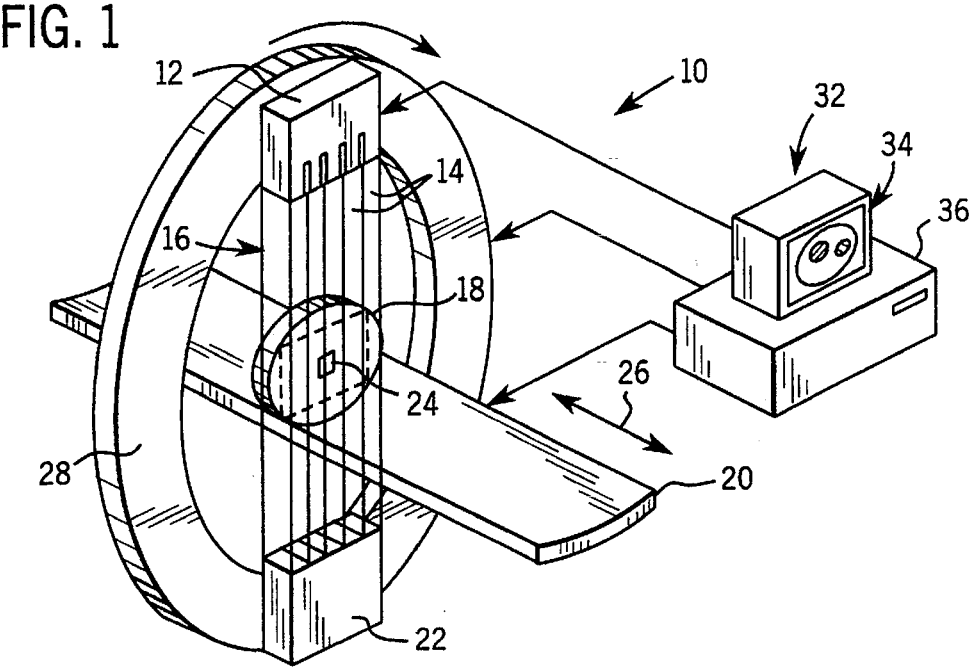
FIG. 1 is a simplified perspective view of a radiotherapy machine producing a plurality of pencil beams of radiation independently controllable by an electronic computer as may be used with the present invention.

Referring now to FIG. 1, an example radiation therapy system 10, such as can be used with the present method, provides a radiation source 12 directing a fan beam 16, composed of a plurality of adjacent "pencil" beams 14, through a treatment volume 18 and a radiation transparent table 20 supporting the treatment volume 18. The individual beams 14 passing through the treatment volume 18 and table 20 are received by a stop 22 generally opposite the radiation source 12 with respect to the treatment volume 18.

The treatment volume 18 is typically a "slice" of a patient; however, the table 20 may be moved along its longitudinal axis 26 so that multiple slices of a patient can be irradiated to treat an arbitrary volume of the patient. The treatment volume 18 may be thought of as divided into a number of generally rectangular volume elements ("voxels") 24 which, for convenience, are substantially the width of one beam 14 and the thickness of one slice.

The radiation source 12 and stop 22 are mounted on a gantry 28 which may rotate to move the radiation source 12 and stop 22 in opposition to orbit the treatment volume 18 so that the fan beam 16 may irradiate the treatment volume 18 at a variety of different angles. The dose of radiation received by each voxel 24 is the sum of the doses received by the voxel at each angle of the gantry 28.

As the gantry 28 rotates, the intensity of each pencil beam 14 of the fan beam 16 may be independently controlled. One method of controlling the intensity of such beams is described in U.S. Pat. No. 5,317,616 described above and hereby incorporated by reference. In this method, radio-opaque shutters are inserted in the path of the pencil beams 14 for varying durations of time to control the intensity of each beam.

By controlling the intensities of the beams 14 ("the beam weights") at different angles of the gantry 28, the summing together of the doses produced by beams 14 at the different gantry angles can produce accurate and complex cumulative radiation doses within the treatment volume 18. An electronic computer 32 controls the radiation source 12 to provide the necessary beam weights and controls the rotation of the gantry 28 and movement of the table 20. The computer 32 includes a display 34 together with a keyboard (not shown) providing for user input and output and a processing unit 36 for performing the necessary calculation to be described.

Planning Method Overview

Figure 2:
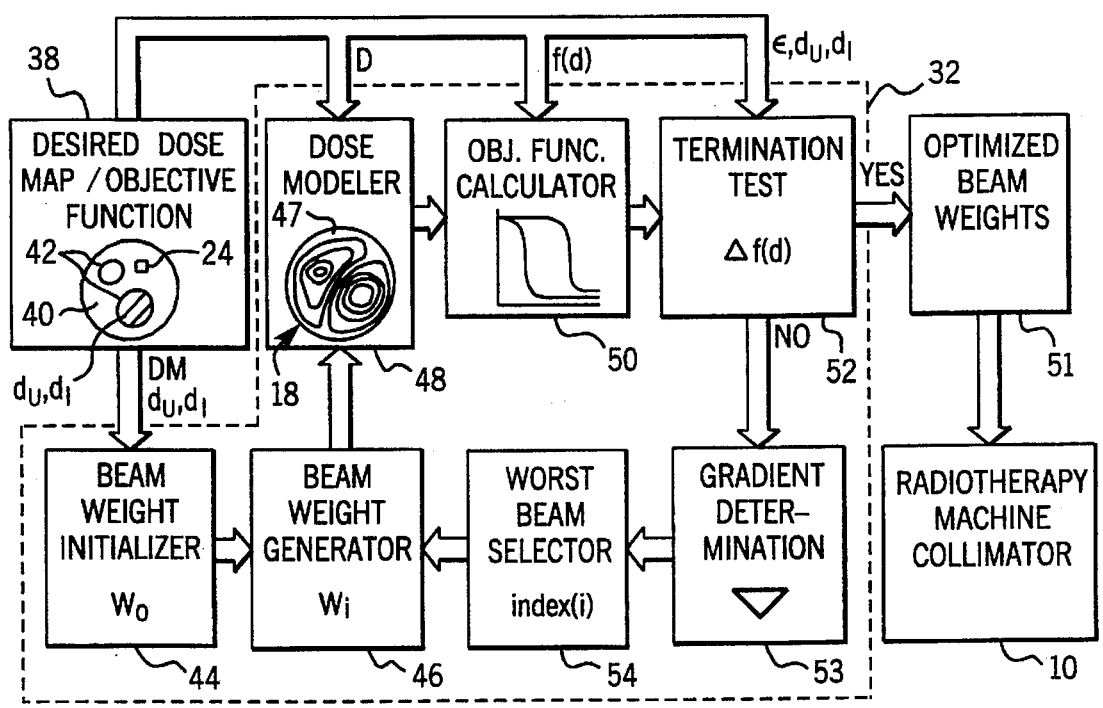
FIG. 2 is a block diagram of the steps performed by the electronic computer of FIG. 1 in determining the intensities of the pencil beams for a desired dose map and objective function.

Referring now to FIG. 2, a radiation planning session begins as indicated by block 38 with a user entering parameters defining the desired distribution of dose within the patient volume 18 and an objective function, f(d), which quantifies how good a particular dose pattern is, and is generally a function of the computed dose $d_i$.

Objective functions may be placed broadly into two classes: (1) physical objective functions, for example, one minimizing the least square error between a computed dose distribution and a desired dose distribution and (2) so-called biological objective functions that minimize the probability of normal tissue complications (as opposed to actual dose) while maximizing the probability of tumor control. Biological objective functions require an understanding of the effect of given dose on the biological tissue.

One possible physical objective function is that of least squares taking the form of $\frac{1}{2}(d_i-d_p)T(d_i-d_p)$ where $d_i$ and $d_p$ are matrix elements (described below) which represent the desired computed dose respectively, and where the T superscript is a matrix transposition operator. Another example is a "dose volume histogram" or DVH which provides a function indicating dose versus percentage of the voxels 24 receiving that dose or less and thus provides a measure of the "sharpness" of a computed dose map 47. Normally, the DVH includes two measures, one considering DVH only for tumorous tissue, and one considering DVH only for radiation sensitive tissue. Thus, the quality of the treatment planning is defined by the DVH which provides a quick indication of how much tumorous tissue is not receiving the minimum necessary dose level and how much sensitive tissue is receiving more than the desired dose level. It will be understood to those of ordinary skill in the art that other objective functions may also be used.

Referring still to FIG. 2, after the desired dose map/objective function has been input by the user, the various components of that desired dose map/objective function 38 are distributed to various processes implemented by the processing unit 36 according to a stored program.

After the desired dose map/objective function 38 has been entered, the optimization process selects an initial set of beam weights $w_0$ for each gantry angle. These beam weights may be chosen in a number of ways, some of which will be described below.

In the first pass of the iterative process, the initial weights $w_0$ become current weights $w_i$ for each of the beams as indicated by process block 46. These beam weights $w_i$ are then passed to the dose modeler 48 and a dose is calculated for the treatment volume 18 based on those beam weights $w_i$. The dose modeler 48 employs the matrix D as previously input by the user and will also be described in more detail below.

Generally, this dose is then passed to the objective function calculator 50 which computes the objective function f(d) as previously input by the user.

Next at a termination testing block 52, the change in the objective function $\Delta f(d)$ is tested to see if it is acceptable according to criterion to be described below. If so, the beam weights $w_i$ become the optimized beam weights as indicated by process block 51 and are output in the form of a sinogram to the radio therapy machine collimator 10 for use in the treatment.

Normally, in the initial stages of this process, the objective function will not meet the termination criterion and the process will proceed to process block 53 and the gradient of the objective function, $\nabla f(d_i)$, as a function of beam weights is computed.

This gradient is used at process block 54 to select one or more beams that have the greatest effect on the objective function. These beams are preferentially changed at the beam weight generator 46, as will also be described below. The process of process blocks 48, 50 and 52 is repeated until the objective function passes the termination test at process block 52.

An Example Using A Least Squares Objective Function

For clarity in the following description, the process of these blocks will be described in detail for the objective function of the least square error between the desired dose map 38 input by the user and the actual dose modeled at the dose modeler 48.

User Input Parameters

As mentioned above, the user must input certain parameters defining the desired dose and the equipment being used. These parameters generally include: 1) a description of tissue characteristics affecting how dose is absorbed by different volume elements 24 of the tissue in the form of an array D, 2) an objective function, f(d), serving to quantify how well the beam weights selected meet clinical requirements defined by the user, 3) criteria for terminating the beam weight adjustment process, for example, a threshold $\epsilon$ below which changes in the objective function are considered insignificant and an acceptable solution is considered reached, 4) upper and lower dose limits $d_u$, $d_l$ for each voxel which define an acceptable range of dose in each voxel of the irradiated volume and the desired dose $d_i$ for each voxel defining the spatial distribution of dose.

Also included in the desired dose map/objective function 38 are parameters describing the radiotherapy machine 10 and physical aspects of the treatment protocol including how many different independently controllable beams 14 are available and how many angles of the gantry 28 will be employed during the treatment session. In addition, a value k is provided indicating the number of different discrete intensity levels obtainable or desirable in controlling each beam. k is an exponent of 2 and thus the actual number of beams will be $2^k$.

Generation of these necessary parameters starts with the acquisition of a CT data set 40 indicating the general region of interest to be irradiated. The physician may trace one or more areas 42 on the image of the CT data set and assign to these areas different dose values, normally by providing a range of dose values between the upper limit $d_u$ and a lower limit $d_l$. The CT data is also used to prepare the array D because the tissue characteristics revealed by the CT data can provide information on how a dose from individual pencil beams is scattered in the patient.

Selection of Initial Beam Weights

Referring still to FIG. 2, after the desired dose map and objective function and other parameters have been entered at block 38, the initial beam weights are selected at block 44. Beam weights can be initialized by several methods. First, constant uniform values such as zero or one may be selected for each beam weight. Alternatively, random non-uniform values may be selected. In a preferred embodiment, a projection of the desired dose map along the angle of the beams is used to set the initial beam weights. The projection is simply a line integral through the desired dose map along the central ray of each pencil beam 14 at a given angle. The subsequent beam weighting can be modified by convolution filtering to remove physical and geometrical blurring processes such as those described in An iterative filtered backprojection inverse treatment planning algorithm for tomotherapy by Holmes, *Int. J. Rad. Oncol. Biol. Phys.*, 32 (4):1215–1225, (1995), hereby incorporated by reference. The final step in initializing the beam weights $w_0$ is to truncate continuous values to discrete values according to the value k previously entered by the user.

Dose Modeler

Referring to FIGS. 2 and 3, the step of computing a computed dose map requires that the passage of each radiation beam 14 through the material of the treatment volume 18 be modeled. This process is normally complicated by the fact that the beams experience significant scattering as they pass through tissue.

The present invention exploits the fact that the scattering process is independent of the beam weight to pre-compute the scattering and thus to eliminate this computational step during the iterative process of process blocks 44, 46, 48 and 50. As shown in FIG. 3 for each radiation beam 14 (e.g., beam j), being part of the fan beam 16 illuminating the treatment volume 18, a standard dose map 54 is created having voxels 1 through n corresponding to each voxel 24 of the treatment volume 18.

The value of each standard dose element $D_{kj}$ (where k=1 to n) will be the dose expected at the corresponding voxel 24 of the treatment volume 18 if the single beam j illuminates the treatment volume 18, with beam j having a normalized intensity or beam weight $w_j$ of 1. Generally, the voxels directly in line with the beam j will have higher doses with the dose pattern fanning out to lower values reflecting scatter of the radiation.

There are a number of methods of computing radiation scatter within tissue for a single beam, for example" Wong, J. H. and Purdy, J. "On Methods Of Inhomogeneity Corrections For Photon Transport" *Med. Phys* 17(5):807–814 (1990). The density of the tissue through which the radiation travels may be obtained from a CT scanner to more accurately model such scatter. Once a standard dose map 54 has been computed for each individual beam j having a normalized beam weight of 1, the computed dose map 47 for any set of beams 1 to m having arbitrary weights may be rapidly computed by scaling the standard dose maps 54 for each such beam by the actual beam weights and summing together corresponding voxels of the standard dose maps 54. Hence, a cumulative dose $d_i$ for any given voxel 24 of the treatment volume 18 will simply be the sum of the corresponding standard doses $d_i$ times the actual beam weights for those standard doses according to the following formula.

$$d_i = \sum_{j=1}^{n} D_{ij} w_j \tag{1}$$

Alternatively, expressed in matrix formulation, the total dose is:

$$\begin{bmatrix} d_1 \\ \cdot \\ \cdot \\ \cdot \\ d_n \end{bmatrix} = \begin{bmatrix} D_{11} & D_{1j} & D_{1m} \\ \cdot & \cdot & \cdot \\ \cdot & \cdot & \cdot \\ \cdot & \cdot & \cdot \\ D_{n1} & D_{nj} & D_{nm} \end{bmatrix} \begin{bmatrix} w_1 \\ \cdot \\ \cdot \\ \cdot \\ w_m \end{bmatrix} \tag{2}$$

Referring to FIG. 4, the various standard dose maps 54 for each beam 14 (1 to m) are shown superimposed to indicate how the values $D_{ij}$ of corresponding voxels of the standard dose maps are summed to produce the value of the total dose $d_i$ for a voxel 24 of the treatment volume 18. It will be understood that computing a new computed dose map 47 of total doses $d_i$ using a new set of beam weights $w_1$ through $w_m$ involves no more than n×m multiplications and additions and can be rapidly performed without the need for the elaborate computation of scatter at each step of the iteration. For multiple gantry angles this process is simply repeated and the values $d_i$ for each gantry angle are summed together.

The computed dose map 47 may be displayed on the display 34, for example, as a set of iso-dose lines indicating the dose received by each voxel in the treatment volume 18. Alternatively, a shading or coloring system may be employed to illustrate the underlying dose numbers associated with each voxel 24.

Objective Function Calculator

The objective function is next calculated at process block 50 according to a least squares criterion as follows:

$$f(d) = \tfrac{1}{2}(d_r - d_p)^T (d_r - d_p)$$

where $d_i$ and $d_p$ are matrix elements which represent the desired dose map entered by the user and the computed dose determined at block 48, respectively and the T superscript is a matrix transposition operator.

Specifically, the objective function is the sum of the magnitude of the difference between individual voxels of the desired dose map 42 and the computed dose map 47:

$$e = \sum_{i=1}^{n} (dd_i - cd_i)^2 \tag{3}$$

where:

$dd_i$=is the $i^{th}$ voxel of the desired dose map;

$cd_i$=is the $i^{th}$ voxel of the computed dose map; and n is the number of voxels in the desired and computed dose maps.

Termination Test

The difference between the objective function last determined and the current value of the objective function (no test is performed on the first iteration but it is assumed that the iteration does not terminate) is then computed and if it is less than the value of ε previously entered by the user, and if the calculated dose from block 48 is evaluated to see that each of the dose values $d_i$ is within the range $d_u$ to $d_l$ for that particular voxel, the current beam weights are adopted at process block 51, otherwise the program proceeds to process block 53.

Gradient Determination/Worst Beam Selection

If the termination criteria have not been met, a determination must be made as to whether to accept certain of the beam weights and which beam weights to change. If the decision is made to reject one or more beam weights, the present invention contemplates that more efficient execution may be obtained by preferentially adjusting beam weights in beams that have a greater effect on the objective function, in contrast to the purely random selection of which beams to change.

For a general objective function, the beam weight making the greatest contribution to the objective function may be determined by calculating the gradient of the objective function with respect to each beam. For the least square error function this may be accomplished as follows: first an error map may be calculated which preserves the spatial distribution of the mismatch between the desired and calculated dose:

$$e_i = (dd_i - cd_i)^2 \qquad (4)$$

where $e_i$ is the value of the error map 55 for each voxel $i$ of the error map. A beam error value $b_j$ ($j$=1 to m) may be determined by multiplying the error value $e_i$ of the error map 55 by the corresponding standard dose values $D_{ji}$ for each voxel of a given standard dose map 54 per equation (5):

$$b_j = \sum_{i=1}^{n} (D_{ij})^T e_i \qquad (5)$$

The values $b_j$ for each beam $j$ can then be compared to determine which beam 14 most effects the objective function. This beam or several beans having the highest beam error values are preferentially modified in its weight to accelerate initial iterations rapidly toward the solution.

Beam Weight Generator

Many radiation therapy systems 10, either by mechanical design or as a practical matter, can provide only a limited number of different weights for any beam 14. For this reason, the present invention uses a "discretization" of the weights to a few selected values rather than a continuous range of values. This discretization is accomplished during the optimization process by representing the beam weights as a binary number of limited length. For example, each beam weight w may be represented by a 5 digit binary number providing 32 different discrete values of intensity. Only changes in beam weights that result in beams 14 having one of these 32 different discrete values are accepted.

This discretization of the beam weights may be represented mathematically by equation (6).

$$\begin{bmatrix} w_1 \\ \cdot \\ \cdot \\ \cdot \\ w_m \end{bmatrix} = K \begin{bmatrix} B_{11} & \ldots & B_{1(k+1)} \\ \cdot & & \cdot \\ \cdot & & \cdot \\ \cdot & & \cdot \\ B_{m1} & \ldots & B_{m(k+1)} \end{bmatrix} \begin{bmatrix} 2^0 \\ \cdot \\ \cdot \\ \cdot \\ 2^k \end{bmatrix} \qquad (6)$$

where the matrix B has values which are either 0 or 1; K is a scaling factor; and k is the power of 2 or the number of binary digits necessary to express the discrete intensity levels.

Now the dose calculation is given by equation (7) which combines equations (2) and (6):

$$\begin{bmatrix} d_1 \\ \cdot \\ \cdot \\ \cdot \\ d_n \end{bmatrix} = \begin{bmatrix} D_{11} & D_{1j} & D_{1m} \\ \cdot & & \cdot \\ \cdot & & \cdot \\ \cdot & & \cdot \\ D_{n1} & D_{nj} & D_{nm} \end{bmatrix} K \begin{bmatrix} B_{11} & \ldots & B_{1(k+1)} \\ \cdot & & \cdot \\ \cdot & & \cdot \\ \cdot & & \cdot \\ B_{m1} & \ldots & B_{m(k+1)} \end{bmatrix} \begin{bmatrix} 2^0 \\ \cdot \\ \cdot \\ \cdot \\ 2^k \end{bmatrix} \qquad (7)$$

and the changing of beam weights may be performed simply by toggling values of the matrix B from 1 to 0 or vice versa.

As described so far, the process of FIG. 2 may be performed simply by random toggling of values in matrix B to generate new beam weights w and the checking of the change in objective function to determine whether those new beam weights should be retained or discarded. After a number of iterations, a set of beam weights falling within the discrete beam weight values will be determined. Yet no computational effort will have been devoted to computing beam weights to a resolution which would ultimately be discarded. Thus, the iterative process may be more efficient.

A preference in which beams will have their weight changed may be expressed either by making changes only in this particular beam to the exclusion of others or by biasing the random selection of beams according to the values $b_j$. For example, if the value $b_j$ for a first beam is twice as great as that for a second beam, then the modification of the beam weights for the first beam might be performed twice as often as modification of the beam weights for the second beam.

The columns of matrix B in equation (7) represent the numerical places in the binary representation of the beam weights. Thus, toggling in the values of B in the rightmost columns effects a greater change in the beam weights than toggling in the values B in the leftmost columns.

As was described above, the present invention further recognizes that a completely random distribution of toggling of the bits among columns of the matrix B may not be optimal. Instead, in the present invention greater changes in the beam weights maybe preferred over lesser changes in the beam weights in some cases. However, all changes are still ultimately modified by a declining temperature value according to the normal simulated annealing techniques.

This biasing is preferentially performed by selecting a random number between 1 and $2^K - 1$ (e.g., 31 in the example of K=5 bit beam weights). The place of the highest order bit in the binary representation of this randomly selected number determines which column of the matrix B will have its value toggled. Thus, for example, the rightmost column will have its value toggled if the random number selected is anywhere between 16 and 31 inclusive (e.g., 16 different numbers), whereas the second column from the left will have its value toggled for the much smaller range from 8 to 15. Accordingly, the rightmost columns of matrix B will receive substantially more toggling than the leftmost columns of matrix B.

Referring still to FIG. 2, after a number of iterations of processes 44, 46, 48 and 50, a final set of beam weights is output to the display 34 as indicated by block 52. These beam weights for each gantry angle are termed a sinogram and used to control the radiation source 12 and gantry 28 during the radiation treatment procedure.

It will be recognized that this technique will be useful for many types of radiation therapy and is not strictly limited to x-rays nor to a fan beam type system as disclosed in FIG. 1, but that it may be used in any system that provides for multiple beam weights which may be adjusted independently, including area beam exposure systems or those systems where variable scanning rates determine the intensity of effective beams.

In order to apprise the public of the various embodiments that may fall within the scope of the invention, the following claims are made.

I claim:

1. A method of planning radiation treatment of a treatment volume of a patient using a radiation therapy machine generating a plurality of radiation beams to be directed through different parts of the volume, the beams having independently controllable intensities, the method comprising the steps of:

operating an electronic computer according to a stored program to:
   1) pre-compute a standard dose map for a plurality of volume elements within the treatment volume for each beam, under the assumption that the beams have a predetermined normal beam intensity;
   2) receive from a user an objective function indicating a desired distribution of dose the plurality of volume elements within the treatment volume;
   3) scale the standard dose map for each beam by a current weight for that beam and sum the scaled standard dose maps together to produced a computed dose map;
   4) evaluate the computed dose according to the objective function;
   5) adjust the current weight of at least one beam according to the evaluation of step (4) and repeat steps (3) through (5) until the value of the objective has stabilized; and
   6) at the conclusion of step (5) output the adjusted current beam weights as a radiation treatment plan.

2. The method of claim 1 wherein step (1) includes the steps of:
   (i) reading computed tomography data indicating the tissue characteristics in the volume;
   (ii) computing scatter of the beam caused by the tissue characteristics in the volume in determining the standard dose maps.

3. The method of claim 1 wherein the objective function is the least squared error between a computed dose distribution and a desired dose distribution.

4. A method of planning radiation treatment of a treatment volume, of a patient using a radiation therapy machine generating a plurality of radiation beams to be directed through different parts of the volume, the beams having independently controllable intensities, the method comprising the steps of:

operating an electronic computer according to a stored program to:
   1) receive from a user a limited set of discrete intensity values to which each beam will conform;
   2) receive from a user an objective function indicating a desired distribution of dose in the plurality of volume elements within the treatment volume;
   3) compute from a current weight for each beam, a computed dose map;
   4) evaluate the computed dose according to the objective function;
   5) adjust the current weights of the beams according to the evaluation of step (4) to different ones of the discrete intensity values and repeat steps (3) through (5) until the value of the objective has stabilized; and
   6) output the adjusted beam weights as a radiation treatment plan.

5. The method of claim 4 wherein step (5) includes the steps of:
   (i) determining a gradient of the objective function with respect to beam weights;
   (ii) identifying from the gradient at least one beam having the greatest effect on the objective function; and
   (iii) preferentially adjusting the weight of the beam determined in step (ii).

6. The method of claim 4 wherein step (5) preferentially adjusts the current weights among discrete intensity values that cause greater change in the beam weight.

7. The method of claim 4 wherein step (3) includes the steps of:
   (i) pre-computing a standard dose map for a plurality of volume elements within the treatment volume for each beam under the assumption that the beams have a predetermined normal beam intensity; and
   (ii) scaling the standard dose map for each beam by the current weight for that beam and summing the scaled standard dose maps together to produce a computed dose map.

8. The method of claim 4 wherein step (5) includes the steps of:
   (i) representing the current weights as binary numbers having a limited number of bits; and
   (ii) toggling the state of a selected bit in a selected binary number.

9. The method of claim 8 wherein the selected bit is determined by choosing a random number between 0 and $2^n-1$, n being an integer where $2^n$ equals the limited set of discrete intensity values and selecting the bit equal to the highest bit in the binary representation of the random number;
   whereby higher order bits are preferentially toggled.

10. The method of claim 4 wherein step (5) determines a gradient of the objective function with respect to beam weights and uses the gradient to preferentially adjust the weights of beams having the greatest effect on the objective function.

11. A radiation treatment system comprising:
    a radiation source generating a plurality of radiation beams to be directed through different parts of a treatment volume, the beams having independently controllable intensities according to a control signal; and
    an electronic computer according to a stored program to:
    1) pre-compute a standard dose map for a plurality of volume elements within the treatment volume for each beam, under the assumption that the beams have a predetermined normal beam intensity;
    2) receive from a user an objective function indicating a desired distribution of dose in the plurality of volume elements within the treatment volume;
    3) scale the standard dose map for each beam by a current weight for that beam and sum the scaled standard dose maps together to produce a computed dose map;
    4) evaluate the computed dose according to the objective function;
    5) adjust the current weight of at least one beam according to the evaluation of step (4) and repeat steps (3) through (5) until the value of the objective has stabilized; and
    6) at the conclusion of step (5) output the adjusted current beam weights as a radiation treatment plan.

12. A radiation treatment system comprising:
    a radiation source generating a plurality of radiation beams to be directed through different parts of a treatment volume, the beams having independently controllable intensities according to control signal; and
    an electronic computer according to a stored program to:

1) receive from a user a limited set of discrete intensity values to which each beam will conform;
2) receive from a user an objective function indicating a desired distribution of dose in the plurality of volume elements within the treatment volume;
3) compute from a current weight for each beam, a computed dose map;
4) evaluate the computed dose according to the objective function;
5) adjust the current weights of the beams according to the comparison of step (4) to different ones of the discrete intensity values and repeat steps (3) through (5) until the value of the objective has stabilized; and
6) output the adjusted beam weights as a radiation treatment plan.

* * * * *

UNITED STATES PATENT AND TRADEMARK OFFICE
CERTIFICATE OF CORRECTION

PATENT NO. : 5,647,663

DATED : July 15, 1997

INVENTOR(S) : Timothy W. Holmes

It is certified that error appears in the above-identified patent and that said Letters Patent is hereby corrected as shown below:

Col. 2, line 10, "$(-\Delta f(a)/T)$"   Should be --$(-\Delta f(d)/T)$--.

Col. 2, line 11, "$\Delta f(a)$"   Should be --$\Delta f(d)$--.

Col. 3, line 26,
optimization B process   Should be --optimization process--

Signed and Sealed this

Twenty-fourth Day of February, 1998

*Attest:*

BRUCE LEHMAN

*Attesting Officer*   *Commissioner of Patents and Trademarks*